(12) United States Patent
Allen (10) Patent No.: US 10,661,024 B2
(45) Date of Patent: May 26, 2020

(54) TWO PIECE NEEDLE SHIELD PULLER

(71) Applicant: West Pharmaceutical Services, Inc., Exton, PA (US)

(72) Inventor: Timothy Allen, Scottsdale, AZ (US)

(73) Assignee: West Pharmaceutical Services, Inc., Exton, PA (US)

(*) Notice: Subject to any disclaimer, the term of this patent is extended or adjusted under 35 U.S.C. 154(b) by 677 days.

(21) Appl. No.: 15/078,379

(22) Filed: Mar. 23, 2016

(65) Prior Publication Data

US 2017/0274151 A1  Sep. 28, 2017

(51) Int. Cl.
*A61M 5/32* (2006.01)

(52) U.S. Cl.
CPC ........ *A61M 5/3204* (2013.01); *A61M 5/3202* (2013.01); *A61M 5/3213* (2013.01); *A61M 2005/3215* (2013.01); *A61M 2005/3217* (2013.01)

(58) Field of Classification Search
CPC .............. A61M 5/3204; A61M 5/3202; A61M 5/3213; A61M 5/3137; A61M 5/3134; A61M 5/31511; A61M 2205/586; A61M 2005/3139
See application file for complete search history.

(56) References Cited

U.S. PATENT DOCUMENTS

| | | | |
|---|---|---|---|
| 1,910,750 A * | 5/1933 | Clark | B25B 7/02 81/417 |
| 5,143,414 A * | 9/1992 | Rosellini | A61M 5/3213 128/919 |
| 2009/0182284 A1 * | 7/2009 | Morgan | A61M 5/3137 604/198 |
| 2013/0289489 A1 | 10/2013 | Evans et al. | |

FOREIGN PATENT DOCUMENTS

| | | |
|---|---|---|
| EP | 2705865 A2 | 3/2014 |
| WO | 2014031521 A1 | 2/2014 |
| WO | 2015048791 A1 | 4/2015 |

OTHER PUBLICATIONS

Extended European Search Report dated Aug. 14, 2017 in EP Application No. 17162478.6.

* cited by examiner

*Primary Examiner* — Nathan R Price
*Assistant Examiner* — Justin L Zamory
(74) *Attorney, Agent, or Firm* — Panitch Schwarze Belisario & Nadel LLP (57) ABSTRACT

A needle shield remover for removing a needle shield covering a needle on a syringe includes a body having a proximal portion and a distal portion. The distal portion is moveable between a contracted configuration and an expanded configuration in response to opposite movement of the proximal portion. The distal portion includes an internal opening for receiving and at least partially surrounding a needle shield therein. An anchor extends inwardly from the distal portion into engagement with the needle shield when the distal portion is in the contracted configuration to secure the body to the needle shield. A sleeve is in fixed axial arrangement with the proximal portion of the body. The axial engagement maintains the distal portion of the body in the contracted configuration such that force applied to the sleeve away from the body removes the needle shield and body from a syringe.

25 Claims, 3 Drawing Sheets

TWO PIECE NEEDLE SHIELD PULLER

BACKGROUND OF THE INVENTION

The present invention relates generally to syringes and, more particularly, to a puller tool for removing a needle shield coupled to a syringe.

Hypodermic needles generally include a needle assembly and a needle shield. The needle shield covers the needle assembly prior to use of the syringe to protect the needle from damage caused by outside forces and to protect against inadvertent needle "sticks" prior to and after injection of the medication. The needle shield is removed at the time of use to expose the sharp point of the needle which can inflict injury if the user inadvertently sticks themselves. For example, when a needle shield is held in one hand of a user and the syringe shield in the other hand of the user and the hands are pulled in opposite directions for removal of the needle shield, once the needle shield is removed the user's body reflexes to compensate for the sudden movement caused by the removal. Both of the user's hands, often recoil, directing the exposed needle tip back toward the user's hand that is holding the removed needle shield, sometimes causing the exposed needle tip to inadvertently stick the user. Devices are often used to remove the needle shield from the needle assembly to avoid the risk of inadvertent sticks. Care must be taken when using such devices to avoid damaging the needle shield and the needle assembly while removing the needle shield. There are many different types of needle shields commercially available and a wide variety of devices which may apply a compressive force when removing the needle shield.

It would therefore be advantageous to provide a needle shield puller capable of removing a needle shield while minimizing or eliminating forces exerted while coupling the needle shield puller to the needle shield and while removing the needle shield from the syringe which could result in needle sticks or compromising the syringe sterility by displacing the needle shield in relation to the needle.

BRIEF SUMMARY OF THE INVENTION

Briefly stated, one aspect of the present invention is directed to a needle shield remover for removing a needle shield covering a needle on a syringe and includes a body having a proximal portion and a distal portion. The distal portion is moveable between a contracted configuration and an expanded configuration in response to opposite movement of the proximal portion. The distal portion has an internal opening for receiving and at least partially surrounding a needle shield therein. An anchor extends inwardly from the distal portion into engagement with the needle shield when the distal portion is in the contracted configuration to secure the body to the needle shield. A sleeve is in fixed axial engagement with the proximal portion of the body thereby maintaining the distal portion of the body in the contracted configuration such that force applied to the sleeve away from the body removes the needle shield and body from a syringe.

Another aspect of the present invention is directed to a needle shield remover for removing a needle shield covering a needle on a syringe and includes a body having a proximal end, a distal end, a first leg extending from the proximal end to the distal end, a second leg spaced from the first leg and extending from the proximal end to the distal end, and a living hinge extending between the first leg and the second leg. The living hinge provides relative movement of the body between a contracted configuration wherein the distal end of the first and second legs are separated from each other by a contracted distance and an expanded configuration wherein the distal end of the first and second legs are separated by an expanded distance greater than the contracted distance in response to opposite movement of the proximal ends of the first and second legs. The distal end of the first and second legs define an internal opening for receiving and at least partially surrounding a needle shield therein. An anchor extends from the distal end of each of the first and second legs into engagement with the needle shield when the first and second legs are in the contracted configuration to secure the body to the needle shield. The needle shield remover includes a sleeve with a graspable handle. The sleeve is coaxially fixed with the body at the distal ends of the first and second legs and maintains the distal end of the first and second legs in the contracted configuration such that force applied to the sleeve away from the body removes the body, and thus the needle shield, from a syringe. A catch extends outwardly from at least one of the body and the sleeve. The catch includes a ramp portion to deflect the body as the sleeve engages the body. An aperture latch is formed on the other of the body and the sleeve and the catch is positioned within the aperture latch when the sleeve is in engagement with the distal end of the body to fix the body to the sleeve.

Still another aspect of the present invention is directed to a method of removing a needle shield from a syringe having a needle including positioning a needle shield within a shield puller body while a distal end of the shield puller body is in an expanded state. The method also includes moving the distal end of the shield puller body from the expanded state to a contracted state, thereby coupling the distal end of the shield puller body to the needle shield and slidingly receiving a proximal end of the shield puller body with a sleeve, thereby securing the distal end of the shield puller body in the contracted state. The method includes applying an axial force to the sleeve away from the distal end of the shield puller body, thereby applying the force to the shield puller body and the needle shield to remove the needle shield from the syringe.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments of the needle shield puller which are presently preferred. It should be understood, however, that the invention is not limited to the precise arrangements and instrumentalities shown.

In the drawings.

DETAILED DESCRIPTION OF THE INVENTION

Certain terminology is used in the following description for convenience only and is not limiting. The words "right," "left," "lower," and "upper" designate directions in the drawings to which reference is made. The words "inwardly" or "distally" and "outwardly" or "proximally" refer to directions toward and away from, respectively, the geometric center or orientation of the needle shield puller and related parts thereof. Unless specifically set forth herein, the terms "a", "an" and "the" are not limited to one element but instead should be read as meaning "at least one". The terminology includes the above-listed words, derivatives thereof and words of similar import.

It should also be understood that the terms "about," "approximately," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

The present invention relates to a needle shield remover generally designated 10 as shown in FIGS. 1 to 6. The needle shield remover 10 removes a needle shield 24 covering a needle (not shown) on a syringe 26. The needle shield remover 10 includes a clamp-like body 12 having a generally cylindrical shape with a proximal portion 14 and a distal portion 16. Alternatively, the body 12 can have any cross-sectional shape (e.g. square, rectangular, elliptical, any polygon, etc.). The body 12 is preferably manufactured from a material (e.g. plastic, high density polyethylene (HDPE), metal, or the like) having sufficient strength and rigidity to withstand the forces imparted onto the body 12 during use, as explained in greater detail below.

The body 12, shown in FIGS. 1-6, has a first leg 18 and a second leg 20. Each leg 18, 20 extends from the proximal portion 14 to the distal portion 16. Although reference is made to each of the first and second legs 18, 20 separately, the body 12 is preferably formed as a monolithic element with at least the distal and proximal portion of the first leg 18 and second leg 20 being separated from each other by keyways 21 at their proximal portion 14 and a space 23 at their distal portion 16, as explained in greater detail below. The first leg 18 and second leg 20 are connected to each other by a living hinge 22 between the proximal portion 14 and distal portion 16. The keyways 21 and living hinge 22 preferably extend from a proximal end 34 and distal end 32, respectively, and abut the living hinge 22. The living hinge 22 provides relative movement of the body 12 between a contracted configuration (best seen in FIG. 1) wherein the distal portion 16 of the first leg 18 and second leg 20 are separated by a first distance, and an expanded configuration (best seen in FIG. 4) wherein the distal portion 16 of the first leg 18 and second leg 20 are separated by second distance greater than the first distance. Although the body 12 is preferably manufactured as a monolithic element, the first and second legs 18, 20 and the living hinge 22 can be manufactured as separate elements and then coupled to each other by methods known in the art (e.g. welding, adhesive, screws, anchors, or the like). The living hinge 22, first leg 18, and second leg 20 preferably comprise the same material in FIGS. 1-6, but one or more could be formed of different materials.

Figure 1:
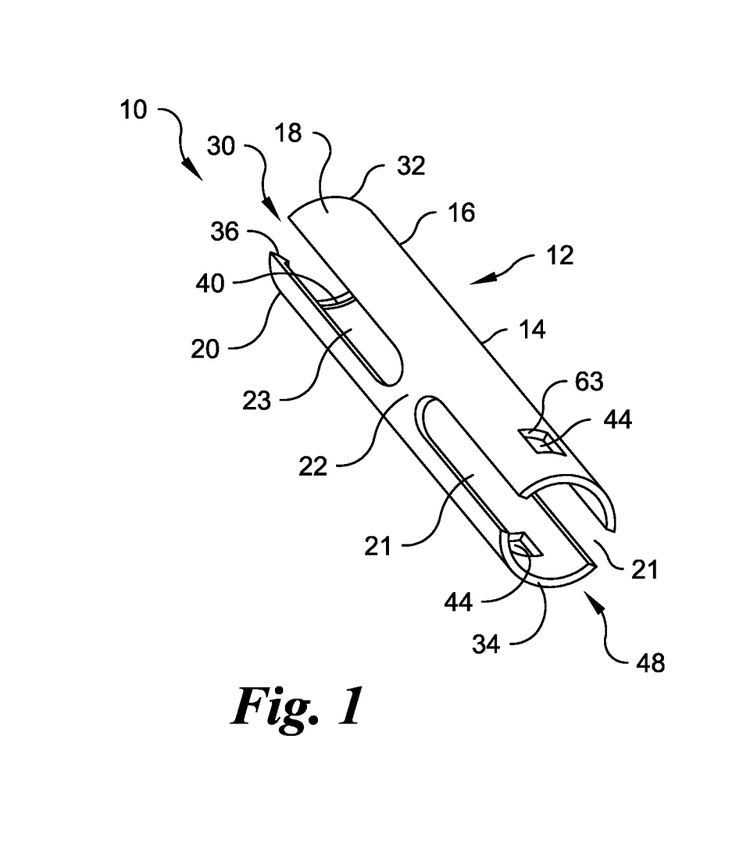
FIG. 1 is a top perspective view of a needle shield remover body in accordance with one embodiment of the present invention.
Figure 2:
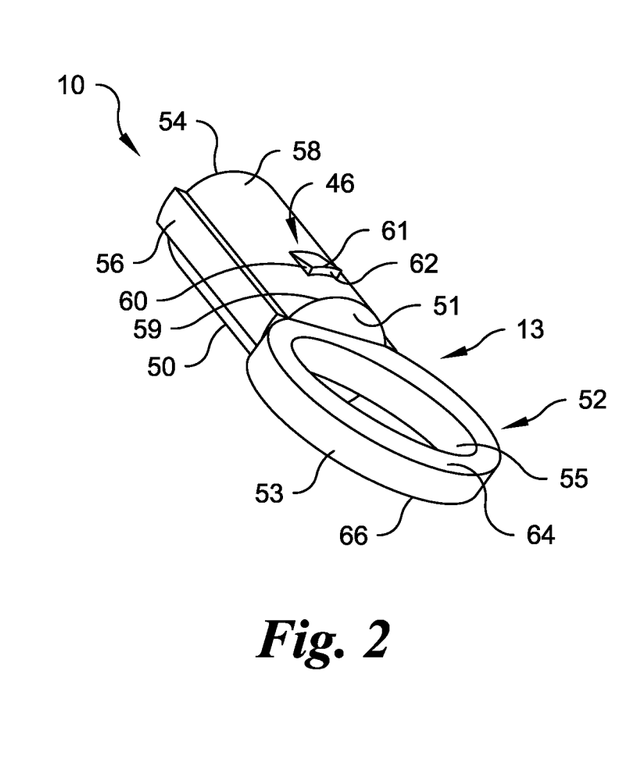
FIG. 2 is a top perspective view of a sleeve in accordance with one embodiment of the present invention.
Figure 3:
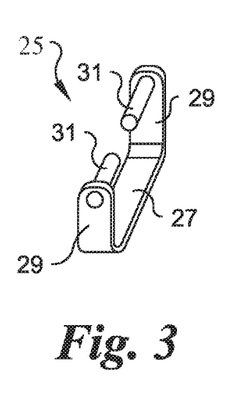
FIG. 3 is a side perspective view of an installation aid in accordance with one embodiment of the present invention.

The distal portion 16 of the first leg 18 and second leg 20 moves between the contracted configuration and expanded configuration in response to opposite movement of the proximal portion 14 of the first leg 18 and second leg 20, for example, by applying a compressive force 28 (FIG. 4) to the proximal portion 14. The keyways 21 between the proximal portion 14 of the first leg 18 and second leg 20 decreases as the compressive force 28 is applied to the proximal portion 14. Alternatively, the keyways 21 could be deformable regions (not shown but could be accordion style folding regions, flexible portions, etc.) provided that the first leg and second leg 18, 20 are able to transition between the expanded state shown in FIG. 4 and the contracted state shown in FIG. 5 without interference between the distal portion 16 of the first leg 18 and the second leg 20. As the keyway 21 decreases, the first leg 18 and second leg 20 pivot about the living hinge 22 such that the distal end 16 of the first leg 18 and second leg 20 expand away from each other increasing the space 23 and the body 12 transitions to the expanded configuration. The living hinge 22 deforms slightly as the force is applied to the proximal end 14 of the body 12. In other words, the first leg 18 and second leg 20 pivot about the living hinge 22 in an operation similar to that of a clothes pin. Alternatively, the living hinge 22 could be any type of hinge or other element which allows relative movement of the proximal portion 14 and distal portion 16 of the body 12 (e.g. ball and socket joint, traditional hinge, rocker, or the like) and need not necessarily deform during operation. The body 12 preferably returns to the contracted configuration as shown in FIG. 1 when the compressive force 28 is removed from the proximal portion 14. Alternatively, the body 12 may be configured to return to the contracted configuration upon application of a compressive force to the distal portion 16 or an expansive force to the proximal portion 14. The living hinge 22 separates the proximal portion 14 from the distal portion 16. The proximal portion 14 and distal portion 16 preferably have equal lengths as shown in FIGS. 1-6, but either could be longer or larger than the other, if desired.

An internal opening 30 extends from the distal end 32 toward the proximal end 34 of the body 12. The internal opening 30 has a generally circular cross-sectional shape, preferably sized slightly greater than the needle shield 24 which the needle shield remover 10 will be used to remove. On advantage of having an internal opening 30 slightly greater in size than the needle shield 24 reduces or eliminates any compressive forces on the needle shield 24 during removal of the needle shield 24 from the syringe 26. Alternatively, the size of the internal opening 30 may be slightly smaller than the needle shield 24 to provide a tight fit when contracted. In other alternatives, the internal opening 30 cross-sectional shape could be square, triangular, oval, elliptical etc. provided that the internal opening 30 is adapted to receive the needle shield 24. The internal opening 30 of FIGS. 1-6 extends completely through the body 12 along a distal to proximal axis (not shown). Alternatively, the living hinge 22 can extend completely through the body, thus limiting the length of the internal opening 30.

The distal end 32 of the internal opening 30 includes an anchor 36 which extends away from the first leg 18 and second leg 20 and into the internal opening 30 for engagement with the needle shield 24. Alternatively, the anchor 36 may extend from only one of the first and second legs 18, 20. The anchor 36 in FIGS. 1-6 is a spur configured to engage the distal end 38 of the needle shield 24. The anchor 36 includes an annular protrusion 40 or ledge such that when the body 12 is in the contracted configuration the annular protrusion 40 has an inner diameter which is at least slightly less than the outer diameter of the needle shield 24. Thus, when an axial force is applied to the body 12 as explained below, the annular protrusion 40 contacts and transfers the force to the distal end 38 of the needle shield 24 to remove the needle shield 24 from the syringe 26. Alternatively, the anchor 36 can be a barb (not shown) extending from or completely through the distal end 32 of the first leg 18 or second leg 20 and penetrating a surface of the needle shield 24 when the body 12 is transferred to the contracted configuration. In yet another alternative, other anchoring elements are incorporated into the needle shield remover body 12 (not shown but could be adhesive, Velcro, ball and detent structure, etc.).

The body 12 includes at least one and preferably two keyways 21 which extend completely through the body 12 and separate the first leg 18 from the second leg 20 in FIGS. 1-6. Alternatively, the keyways 21 could be recesses in the outer wall of the body 12 with a second living hinge (not shown) connecting the proximal portion 14 of the first leg 18 and second leg 20 such that the keyways 21 do not extend completely through the proximal portion 14 but still allow the first and second legs 18, 20 to expand and contract, as desired. The keyways 21 extend in a straight line as they extends from the proximal end 34 toward the distal end 32 and each sized to receive a key 56 formed on the sleeve 13. Alternatively, the keyways 21 could also be arced, angled, or include turns such that the sleeve 13 is rotated when it is inserted to further secure the sleeve 13 to the body 12.

The proximal portion 14 of each of the first leg 18 and second leg 20 includes at least one and preferably two oppositely disposed aperture latches 44 each adapted to receive a catch 46 on the sleeve 13 as explained in greater detail below. Alternatively, the aperture latches 44 could be formed on the sleeve 13 and the catches 46 formed on the of the body 12 (not shown). In yet another alternative (not shown), a combination of the catches 46 and the aperture latches 48 are formed on each of the body 12 and sleeve 13. In still yet another alternative (not shown), the aperture latches 44 or catches 46 could be formed on only one of the first and second legs 18, 20. Each aperture latch 44 is a generally square opening extending through the proximal portion 14 of the body 12 but could be any desired shape (e.g. circle, oval, diamond, star, any polygon) provided that the aperture latches 44 can receive and secure the catches 46 during operation of the needle shield remover 10.

A passageway 48 extends from the proximal end 34 toward the distal end 32 of the body 12 to receive the sleeve 13. The passageway 48 has a diameter sized at least slightly larger than the sleeve 13 to avoid expanding the proximal portion 14, and compressing the distal portion 16, of the first and second legs 18, 20 when the sleeve 13 is inserted into the passageway 48 thus causing a compressive force on the needle shield 24. The passageway 48 of FIGS. 1-6 is the same size as the internal opening 30, but need not necessarily be so. For example, the passageway 48 can be larger or smaller than the internal opening 30 to accommodate a sleeve 13 which is smaller or larger in diameter than the needle shield 24. The internal opening 30 and passageway 48 can have different diameter, lengths, or both. The passageway 48 is generally cylindrical in shape but could be any desired shape provided that the passageway 48 can receive the sleeve 13. The proximal end 34 of the first leg 18 and second leg 20 may be tapered (not shown) to facilitate easier loading of the sleeve 13 into and out of the passageway 48.

The sleeve 13 includes a generally cylindrical base 50 extending from a handle 52. The base 50 and handle 52 may be a monolithic element or, alternatively, separate elements joined together through traditional methods known to one of ordinary skill in the art (e.g., welding, adhesive, screws, etc.). The base 50 is a generally rigid member comprised of a material (e.g. plastic, stainless steel, or other metal) able to withstand any forces exerted on the base 50 by the first leg 18 and second leg 20 during use of the needle shield remover 10. The base 50 diameter is sized to fit within the passageway 48 and prevent the proximal portion 14 of the first leg 18 and second leg 20 from transitioning to the expanded configuration (FIG. 1). Although the base 50 is shown as a cylindrical member, the base can be triangular, square, octagon or any other cross-sectional shape provided that the base 50 fits within the passageway 48. It may be desirable to have a passageway 48 and base 50 that are not circular in cross-section to prevent rotation of the sleeve 13 when the base 50 is inserted into the passageway 48. The distal end 54 of the base 50 is generally flat as shown in FIGS. 1-6. Alternatively, the distal end 54 may be bullet shaped, tapered, etc. to facilitate easier loading of the sleeve 13 into the passageway 48. In yet another alternative (not shown), the base 50 may be hollow such that a portion of a needle shield can be inserted into the base 50 during use, if desired. The length of the base 50 is preferably such that the base 50 terminates prior to the end of the keyways 21 to ensure that each catch 46 can be fully positioned within the aperture latch 44 without interference between the keys 56 and keyways 21. Alternatively, the base 50 could extend to or even past the living hinge 22 when inserted into the passageway 48 provided that the base 50 does not interfere with the needle shield 24 when the body is coupled to the needle shield 24 and the sleeve 13 is inserted into the passageway 48.

At least one and preferably two keys 56 extend radially away from an outer surface 58 of the base 50 and are inserted into the keyways 21 when the sleeve 13 is coupled to the body 12. The height of each key 56 as shown in FIGS. 1-6 is equal to the thickness of the first leg 18 and second leg 20 such that the keys 56 and keyways 21 present an uninterrupted surface extending around the body 12 when the sleeve 13 is coupled to the body 12. Alternatively, the keys 56 may be greater or smaller in height than the thickness of the first leg 18 and second leg 20, if desired. The keys 56 are formed monolithically with the base 50 but could also be separate elements attached to the base 50 by traditional methods known to one of ordinary skill in the art such as welding, adhesive, screws, etc. When the keys 56 are manufactured separately from the base 50 and later attached, the keys 56 and base 50 may comprise different materials to reduce manufacturing costs, manufacturing time, etc. The keys 56 in the keyways 21 guide the catches 46 into the aperture latches 21 when the sleeve 13 is inserted into the passageway 48.

Each catch 46 extends outwardly from the outer surface 58 of the base 50. Each catch 46 is located toward the proximal end 59 of the base 50 but could be positioned at the distal end 54, or anywhere in between, provided that the catch 46 can be inserted into the corresponding aperture latch 44 when the sleeve 13 is coupled to the body 12. Each catch 46 includes a ramp portion 60 extending away from the outer surface 58 of the base 50 to an upright wall 62 at the proximal end 61 of the catch 46. The ramp portion 60 engages and deflects the inner surface of the first or second leg 18, 20 as the sleeve 13 is inserted into the passageway 48. The first and second legs 18, 20 return to the un-deflected position when the catches 46 are within the aperture latches 44. The upright wall 62 engages a perimeter wall 63 with each aperture latch 44 thereby fixing the sleeve 13 within the body 12 when an axial force is applied to the sleeve 13 as explained below. Although the body 12 and sleeve 13 are shown with only two aperture latches 44 and two catches 46, any number of aperture latches and catches could be adopted. Furthermore, the number of aperture latches 44 and catches 46 need not necessarily be equal to allow various orientations of the sleeve 13 to the body 12 as desired. However, the sleeve 13 and body 12 are preferably co-axial when the sleeve 13 is within the passageway 48 regardless of the number and orientation of the aperture latches 44 and catches 46. The catches 46 are manufactured monolithically with the base 50 or, alternatively, can be manufactured as a separate element which is attached to the base 50 after manufacture. The catches 46 may also be deformable such that when the sleeve 13 is inserted into the passageway 48, the first and second legs 18, 20 remain stationery while the catches 46 are compressed toward the outer surface 58 of the base 50 until the catches 46 are aligned with the aperture latches 44 allowing the catches 46 to return to their un-deformed state and allowing the catches 46 to engage the perimeter walls 63 of the aperture latches 44 thereby preventing removal of the sleeve 13 from the passageway 48 when an axial force is applied to the sleeve 13 as explained below.

The handle 52 is a circular member having an annular outer wall 53 and inner wall 55 connected by a generally flat upper side 64 and lower side 66. Alternatively, the upper side 64 or lower side 66 may be rounded, stepped, etc. (not shown) as desired. The handle 52 in FIGS. 1-6 is a ring engageable by the finger or a thumb of a user. Alternatively, the handle 52 could be rectangular, a straight bar, sling, solid member, or other type of handle provided that it is graspable by a user to apply an axial force to the sleeve 13 after it is inserted and locked into the passageway 48. The handle 52 is preferably a rigid element extending from a proximal wall 51 of the base 50 of the sleeve 13. The thickness of the handle 52 is defined by the height of the outer wall 53 and is less than the diameter of the base 50 of the sleeve 13. However, the handle 52 thickness could also be equal to or greater than the diameter of the base 50, if desired. The handle 52 is preferably monolithically formed with the base 50 but could also be separately formed and coupled to the base 50 by adhesive, screws, welding, etc. The handle 52 shown has a smooth surface but could also have any type of texture or adhesive thereon to enhance the grip for a user (e.g. ridges, glue). The handle 52 is aligned with the keys 56 on the sides of the base 50 and assists a user in aligning the keys 56 with the keyways 21, although such alignment is not required. The handle 52 is preferably thicker than the keys 56 when the handle 52 and keys 56 are aligned with one another such that when the sleeve 13 is inserted into the passageway 48, the handle 52 cannot enter either keyway 21 and prevents over insertion of the sleeve 13 into the passageway 48. The upper side 64 defines an upper plane (not shown) which is generally parallel to the proximal to distal axis (not shown) of the base 50. Alternatively, the upper plane (not shown) could be oblique to the proximal to distal axis (not shown) of the base 50, increasing visibility when aligning the keys 56 with the keyways 21.

An installation aid 25 (FIG. 3) prevents transfer of compressive force from the body 12 to the shield 24 by maintaining the spacing of the distal portion 16 of the body 12. The installation aid 25 has a base 27 extending between arms 29. The length of the base 27 can be adjusted as desired but is preferably slightly larger than the diameter of the body 12 to allow the arms 29 to be positioned on opposing sides of the body 12. The arms 29 are shown extending generally perpendicularly away from the base in FIG. 3 but could also be angled, curved, etc. A pin 31 extends from each arm 39 toward the other arm 29. The pins 31 are shaped to fit within the space 23 between the distal portion 16 of the first and second leg 18, 20 of the body 12. The pins 31 prevent the distal portion 16 of the body 12 from compressing when they are in the space 23, for example when the sleeve 13 is inserted into the passageway 48. The pins 31 are shown having a cylindrical shape but could also be any desired shape provided that the pins 31 fit within the space 23.

Figure 4:
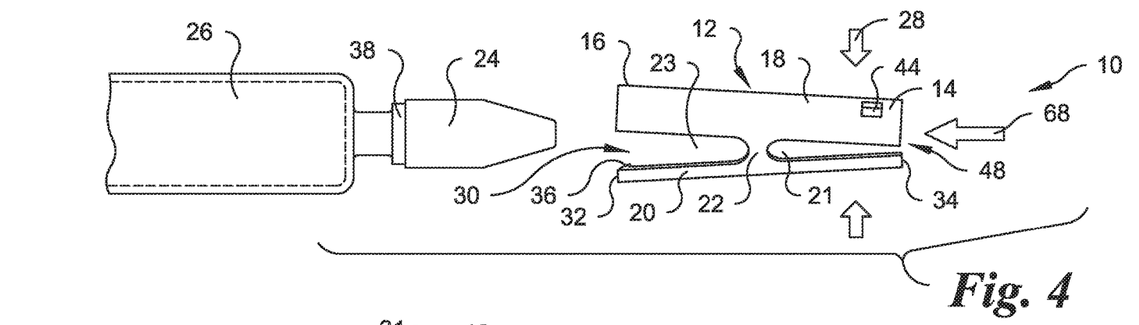
FIG. 4 is a side elevational view of a syringe with a needle shield and the shield puller body of FIG. 1 in an expanded configuration.
Figure 5:
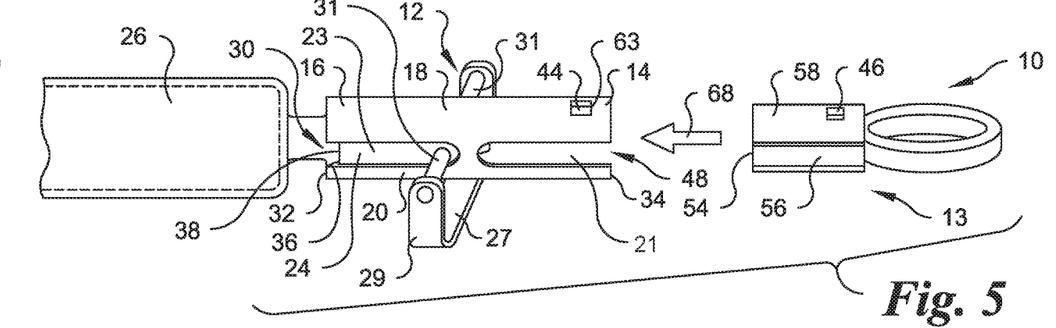
FIG. 5 is a side elevational view of a syringe with a needle shield and the shield puller body of FIG. 1 in a compressed configuration and coupled to the needle shield of FIG. 4 and showing the sleeve of FIG. 2 and the installation aid of FIG. 3.

In use, a user grasps the body 12 and applies a compressive force 28 to the proximal portion 14 (FIG. 4). The compressive force 28 compresses the proximal portion 14 and causes the first leg 18 and second leg 30 to pivot about the living hinge 22 to transfer the distal portion 16 of the body 12 from the contracted configuration shown in FIG. 1 to the expanded configuration shown in FIG. 4 wherein the size of the space 23 between the distal portion 16 of the first leg 18 and second leg 20 is expanded to a greater size than in the contracted configuration. The user then maneuvers the body 12 (se arrow 68 of FIG. 5) relative to the needle shield 24 such that the needle shield 24 enters the internal opening 30. The user continues moving the body 12 in the proximal to the distal direction 68 until the distal end 32 of the body 12, and thus the anchor 36, extends at least slightly past the distal end 38 of the needle shield 24. Alternatively, the distal end 32 of the body 12 need not extend past the distal end 38 of the needle shield 24 if the anchor 36 is a barb as previously discussed because the barb can penetrate the surface of the needle shield 24 anywhere along the length of the needle shield. Once this movement is completed, the user releases the compressive force 28 from the proximal portion 14 of the body 12 thereby allowing the distal portion 16 of the first leg 18 and second leg 20 to counter-rotate about the living hinge 22 to return to the contracted configuration as shown in FIG. 5 such that the inner surface of the first and second legs 18, 20 engages the needle shield 24 and the annular protrusion 40 of the anchor 36 engages the distal end 38 of the needle shield 24.

The user then positions the installation aid 25 such that the pins 31 extend into the space 23 between the distal portion 16 of the first leg 18 and the second leg 20. Alternatively, the user may position the pins 31 in the space 23 prior to releasing the compressive force 28 on the proximal portion 14 of the body 12. The user then grasps the sleeve 13, aligns the keys 56 with the keyways 21 (FIG. 5), and advances the sleeve 13 such that the base 50 enters the passageway 48 and the keys 56 enter the keyways 21. The sleeve 13 may exert a slight expansive force on the proximal portion 14 of the body 12 opposite to the compressive force 28 as the sleeve 13 is inserted into the passageway 48. An expansive force on the proximal portion 14 would cause the distal portion 16 to compress. However, the pins 31 prevent the distal portion 16 from compressing and exerting force on the shield 24. The user continues to advance the sleeve 13 in the proximal to distal direction 68 while the first and second legs 18, 20 slightly deflect from their original position to allow passage of the catches 46. Once the catches 46 are locked within the aperture latches 44, the first and second legs 18, 20 or the aperture latches 44 return to their undeflected position. The sleeve 13 is now axially fixed to the body 12 and cannot be removed (FIG. 6).

Figure 6:
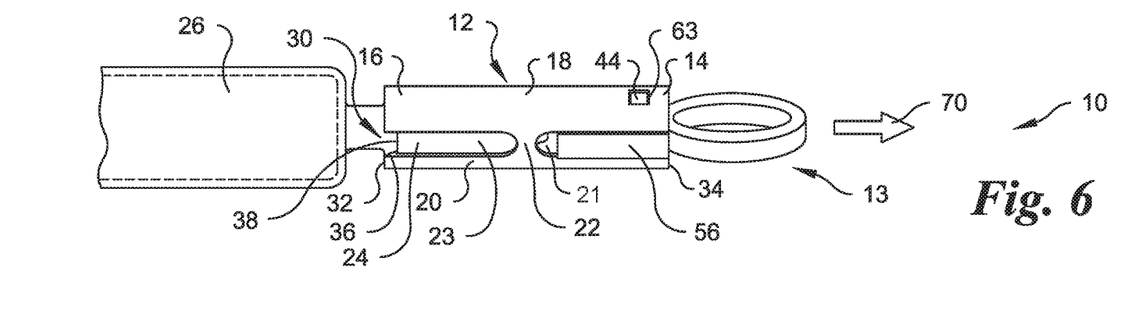
FIG. 6 is a side elevational view of the shield puller body of FIG. 1 in a compressed configuration and coupled to the needle shield of FIG. 4 and the sleeve of FIG. 2 inserted into the body.

The user then engages the handle 52 of the sleeve 13 (while holding the syringe 26) and exerts a force in the distal to proximal direction 70 away from the syringe 26 as shown in FIG. 6. The upright walls 62 engage the perimeter walls 63 of the aperture latches 44, thereby preventing removal of the sleeve 13 such that as the user continues to apply the distal to proximal force 70, the force is applied to the body 12. The body 12 transfers the force to the needle shield 24 via the anchor 36 and the needle shield 24 is removed from the syringe 26. Once the needle shield is removed, the user disengages the catches 46 from the aperture latches 44 thereby allowing removal of the sleeve 13 from the body 12. Once the sleeve 13 is removed from the body 12, the needle shield 24 can be removed from the internal opening 30 by applying the compressive force 28 to the proximal portion 14 of the first and second legs 18, 20 and transferring the distal portion 16 of the body 12 to the expanded configuration. The needle shield remover 10 can then be reused as desired.

The needle shield 24 can be replaced on the syringe 26 after injection of the content to prevent any subsequent needle sticks.

Figures 7, 8, 9:
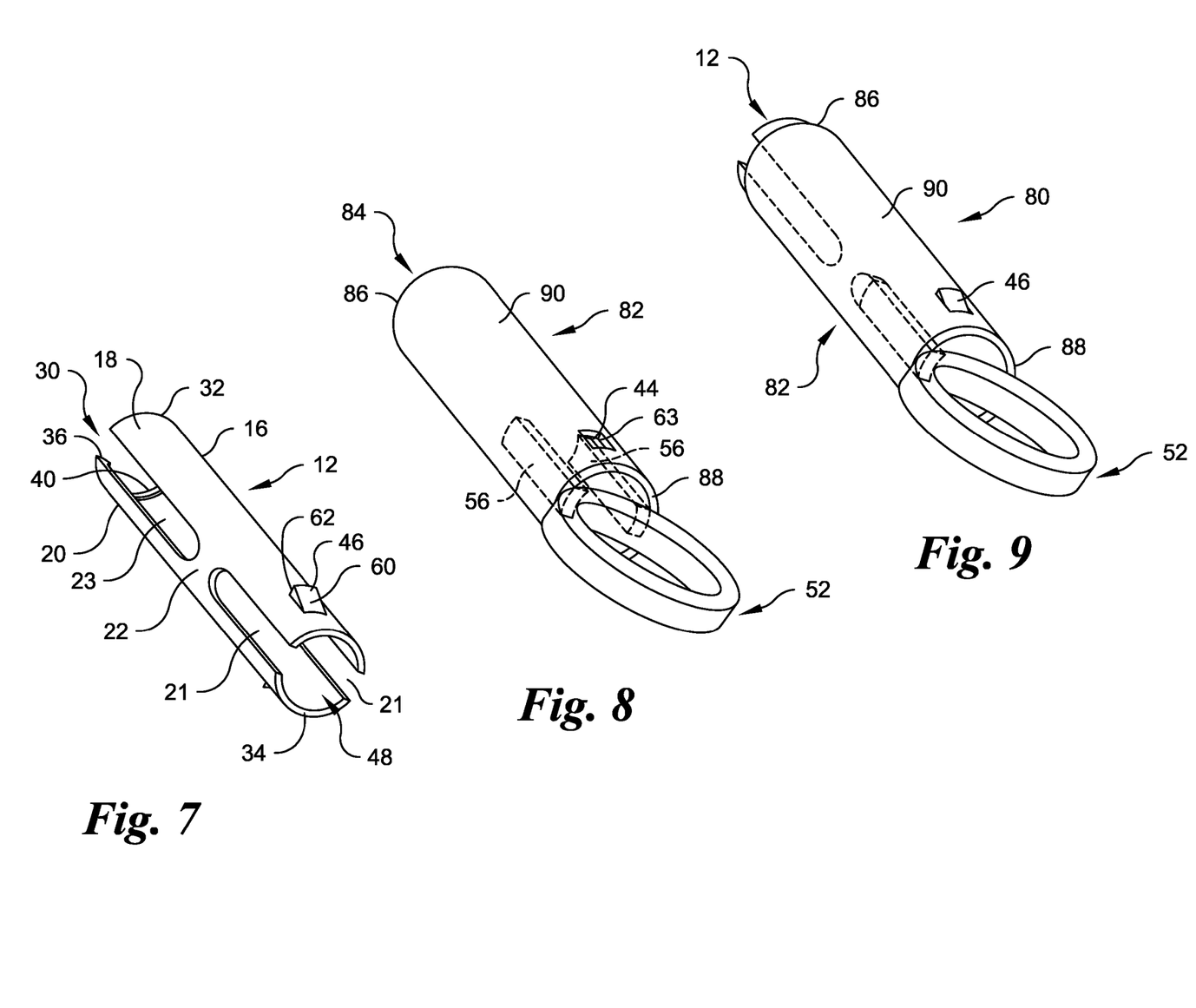
FIG. 7 is a top perspective view of a shield puller body in accordance with another embodiment of the present invention.
FIG. 8 is a top perspective view of a sleeve in accordance with another embodiment of the present invention.
FIG. 9 is a top perspective view of the shield puller body of FIG. 7 inserted into the sleeve of FIG. 8.

Turning now to FIGS. 7-9, another embodiment of a shield puller is shown, generally designated with numeral 80. The shield puller 80 includes some of the same elements as the shield puller 10 embodiment previously described and like reference numbers are used to identify similar elements. Only the differences between the embodiments are discussed here. The body 12 is similar to the body 12 previously described and includes the passageway 48 as shown in FIGS. 7-9. However, the body need not include the passageway 48 because the body 12 does not receive the sleeve 82 within the passageway 48. However, the body 12 still needs to be transferable between the contracted configuration and expanded configuration as previously described.

The shield puller 80 includes a sleeve 82 with a channel 84 extending from a distal end 86 of the sleeve 82 toward a proximal end 88 and adapted to receive the body 12. The channel 84 is preferably slightly larger in diameter than the outer diameter of the body 12. One advantage of having the channel 84 slightly larger than the body 12 is that it avoids any compressive forces on the body 12 and thus the needle shield 24. Alternatively, the channel 84 could be sized to place an acceptable compressive force on the body 12 and thus the needle shield 24 to enhance to coupling of the body 12 to the needle shield 24. The interior of the channel 84 is smooth to facilitate easier insertion of the body 12 into the channel 84 but could also have ratchet teeth, ridges, or other features which allow the sleeve 82 to move with respect to the body 12 in one direction but impede movement in another direction. The length of the sleeve as measured from the distal end 86 to the proximal end 88 is generally equal to the length of the body 12 as measured in the same direction. One advantage of having a sleeve 82 which extends from the proximal end 34 of the body 12 to at least the distal portion 16 of the body 12 is that the sleeve can maintain the distal portion 16 in the contracted configuration after the body 12 is coupled to the needle shield 24. The sleeve 82 could also be shorter or longer than the body 12, if desired.

The keys 56 (shown in phantom in FIGS. 8-9) extend away from the sleeve 82 and into the channel 84 and are inserted into the keyways 21 when the sleeve 82 is engaged with the body 12. The channel 84 preferably extends through the proximal end 88 of the sleeve 82 to allow a user to observe the alignment of the keys 56 with the keyways 21 as the sleeve 82 slidingly engages the body 12. Alternatively, the proximal end 88 of the sleeve could have a solid end wall (not shown) which seals the proximal end 88 of the channel 84. If an end wall (not shown) is formed at the proximal end 88, visual markers (not shown, but could be lines, dots, arrows, laser marks, etc.) can be adopted on the outer wall 90 of the sleeve 82 to assist a user in aligning the keys 56 with the keyways 21.

The sleeve 82 includes the aperture latches 44 as previously described to engage the catches 46 formed on the body 12 in the embodiment shown in FIGS. 7-9. The catches 46 are similar in structure whether attached to the body 12 or the sleeve 13, but the ramp portion 60 faces the proximal end 34 of the body 12 when the catches 46 are formed on the body 12 such that as the sleeve 82 slidingly receives the body 12 within the channel 84, the ramp portion 60 of each catch 46 engages the distal end 86 of the sleeve 82 to deflect the first and second legs 18, 20. The upright walls 62 of the catches 46 face the distal end 32 of the body 12 such that when the catches 46 are within the aperture latches 44, the upright walls 62 engage the perimeter walls 63 of the aperture latches 44 as an axial force is applied to the sleeve 82 in the distal to proximal direction 70. The catches 46 cause the proximal portion 14 of the body 12 to contract slightly as the sleeve 80 receives the body 12 prior to the catches 46 entering the aperture latches 44. Therefore, the anchor 36 is preferably sized such that the corresponding slight expansion of the distal portion 16 of the body 12 does not cause the anchor 36 to disengage from the needle shield 24. Alternatively, the anchor 36 may be allowed to disengage from the needle shield 24 provided that the anchor 36 can reengage the needle shield 24 after returning to the contracted configuration when the catches 46 are within the aperture latches 44. In other alternative embodiments (not shown), the catches 46 and aperture latches 44 could be formed on either of the body 12 and sleeve 82 and any number of catches and aperture latches can be incorporated into either of the body 12 and sleeve 82.

In use, the body 12 engages the needle shield 24 as previously described. The user then slides the sleeve 82 over the body 12 such that the body 12 is positioned within the channel 84 and co-axial with the sleeve. As the user moves the sleeve 82 in the proximal to distal direction 68, the user can observe the alignment of the keys 56 and keyways 21 through the open proximal end 88 of the sleeve 82. The user advances the sleeve 82 relative to the body 12 until the catches 46 are within the aperture latches 44. The user then applies a force to the handle 52, and thus the sleeve 82, axially away from the syringe 26. The force is transferred by the perimeter walls 63 to the upright walls 62 of the catches 46 and to the needle shield 24 by the anchor 36 to remove the needle shield 24. The user can remove the needle shield 24 and reuse the needle shield remover 80 as desired.

It will be appreciated by those skilled in the art that changes could be made to the embodiments described above without departing from the broad inventive concept thereof. It is understood, therefore, that this invention is not limited to the particular embodiment disclosed, but is intended to cover modifications within the spirit and scope of the present invention as defined by the appended claims.

The invention claimed is:

1. A needle shield remover for removing a needle shield covering a needle on a syringe comprising:
    a body having a proximal end, a distal end, a proximal portion situated closer to the proximal end than to the distal end, and a distal portion situated closer to the distal end than to the proximal end, the body being configured so that the distal portion moves between a contracted configuration and an expanded configuration in response to opposite movement of the proximal portion, the distal portion having an internal opening for receiving and at least partially surrounding the needle shield therein, an anchor extending inwardly from the distal portion into engagement with the needle shield when the distal portion is in the contracted configuration to secure the body to the needle shield; and
    a sleeve in fixed axial engagement with the proximal portion of the body thereby maintaining the distal portion of the body in the contracted configuration such that force applied to the sleeve away from the body removes the needle shield and body from the syringe,
    wherein the body is moveable with respect to the needle shield when the body is in the expanded configuration and is fixed to the needle shield when the body is in the contracted configuration.

2. A needle shield remover for removing a needle shield covering a needle on a syringe comprising:
    a body having a proximal end, a distal end, a proximal portion situated closer to the proximal end than to the distal end, and a distal portion situated closer to the distal end than to the proximal end, the body being configured so that the distal portion moves between a contracted configuration and an expanded configuration in response to opposite movement of the proximal portion, the distal portion having an internal opening for receiving and at least partially surrounding the needle shield therein, an anchor extending inwardly from the distal portion into engagement with the needle shield when the distal portion is in the contracted configuration to secure the body to the needle shield; and
    a sleeve in fixed axial engagement with the proximal portion of the body thereby maintaining the distal portion of the body in the contracted configuration such that force applied to the sleeve away from the body removes the needle shield and body from the syringe;
    a keyway on the proximal portion of the body; and
    a key on the sleeve, the key being positioned within the keyway when the body is within the channel.

3. The needle shield remover of claim 1, further comprising:
    a handle coupled to the sleeve, the handle graspable by a user to apply the force to the sleeve to remove the needle shield from the syringe.

4. The needle shield remover of claim 3, wherein the handle comprises a ring engageable with a finger or thumb of a user.

5. A needle shield remover for removing a needle shield covering a needle on a syringe comprising:
    a body having a proximal end, a distal end, a proximal portion situated closer to the proximal end than to the distal end, and a distal portion situated closer to the distal end than to the proximal end, the body being configured so that the distal portion moves between a contracted configuration and an expanded configuration in response to opposite movement of the proximal portion, the distal portion having an internal opening for receiving and at least partially surrounding the needle shield therein, an anchor extending inwardly from the distal portion into engagement with the needle shield when the distal portion is in the contracted configuration to secure the body to the needle shield; and
    a sleeve in fixed axial engagement with the proximal portion of the body thereby maintaining the distal portion of the body in the contracted configuration such that force applied to the sleeve away from the body removes the needle shield and body from the syringe;
    a catch extending outwardly from one of the body and sleeve; and
    an aperture latch on the other of the body and sleeve, the catch being positioned within the aperture latch when the sleeve is in engagement with the distal portion of the body to fix the body to the sleeve.

6. The needle shield remover of claim 5, wherein the sleeve slidingly receives the body and the catch includes a ramp portion to deflect the catch from a first position to a second position as the sleeve slidingly receives the body; and
    wherein the catch returns to the first position when the catch is aligned with the aperture.

7. The needle shield remover of claim 1, wherein the anchor includes at least one of a barb penetrating a surface of the needle shield, and a spur engaging a distal end of the needle shield.

8. The needle shield remover of claim 1, wherein the body is moveable from the contracted configuration to the expanded configuration by applying a compressive force to the proximal portion of the body.

9. A needle shield remover for removing a needle shield covering a needle on a syringe comprising:
    a body having a proximal end, a distal end, a proximal portion situated closer to the proximal end than to the distal end, and a distal portion situated closer to the distal end than to the proximal end, the body being configured so that the distal portion moves between a contracted configuration and an expanded configuration in response to opposite movement of the proximal portion, the distal portion having an internal opening for receiving and at least partially surrounding the needle shield therein, an anchor extending inwardly from the distal portion into engagement with the needle shield when the distal portion is in the contracted configuration to secure the body to the needle shield; and
    a sleeve in fixed axial engagement with the proximal portion of the body thereby maintaining the distal portion of the body in the contracted configuration such that force applied to the sleeve away from the body removes the needle shield and body from the syringe;
    a channel in the sleeve, wherein the body is removably received in the channel when the distal portion of the body is in the contracted configuration.

10. A needle shield remover for removing a needle shield covering a needle on a syringe comprising:
- a body having a proximal end, a distal end, a proximal portion situated closer to the proximal end than to the distal end, and a distal portion situated closer to the distal end than to the proximal end, the body being configured so that the distal portion moves between a contracted configuration and an expanded configuration in response to opposite movement of the proximal portion, the distal portion having an internal opening for receiving and at least partially surrounding the needle shield therein, an anchor extending inwardly from the distal portion into engagement with the needle shield when the distal portion is in the contracted configuration to secure the body to the needle shield; and
- a sleeve in fixed axial engagement with the proximal portion of the body thereby maintaining the distal portion of the body in the contracted configuration such that force applied to the sleeve away from the body removes the needle shield and body from the syringe;
- a passageway in the proximal portion of the body, wherein the sleeve is removably received in the passageway when the distal portion of the body is in the contracted configuration.

11. A needle shield remover for removing a needle shield covering a needle on a syringe, comprising:
- a body having a proximal end, a distal end, a first leg extending from the proximal end to the distal end, and a second leg spaced from the first leg and extending from the proximal end to the distal end, a living hinge extending between the first leg and second leg, the living hinge providing relative movement of the body between a contracted configuration wherein the distal end of the first and second legs are separated from each other by a contracted distance and an expanded configuration wherein the distal end of the first and second legs are separated by an expanded distance greater than the contracted distance in response to opposite movement of the proximal ends of the first and second legs, the distal end of the first and second legs defining an internal opening for receiving and at least partially surrounding a needle shield therein, and an anchor extending from the distal end of each of the first and second legs into engagement with the needle shield when the first and second legs are in the contracted configuration to secure the body to the needle shield;
- a sleeve, including a graspable handle, coaxially fixed with the body at the distal ends of the first and second legs and maintaining the distal end of the first and second legs in the contracted configuration such that force applied to the sleeve away from the body removes the needle shield and body from a syringe;
- a catch extending outwardly from at least one of the body and the sleeve, the catch including a ramp portion to deflect the body as the sleeve engages the body; and
- an aperture latch on the other of the body and the sleeve, the catch being positioned within the aperture latch when the sleeve is in engagement with the distal end of the body to fix the body to the sleeve.

12. The needle shield remover of claim 11, wherein the proximal ends of the first and second legs are separated by a keyway and the sleeve includes a key extending away from the sleeve, the key positioned within the keyway when the body is coaxially engaged with the sleeve.

13. The needle shield remover of claim 11, further comprising at least one of a channel in the sleeve to receive the body and a passageway in the body to receive the sleeve.

14. The needle shield remover of claim 11, wherein the anchor includes at least one of a barb penetrating a surface of the needle shield, and a spur extending away from the distal end of the first and second legs into the internal opening to engage a distal end of the needle shield.

15. The needle shield remover of claim 11, further comprising a reinforcing rib extending outwardly away from at least one of the first and second legs.

16. A method of removing a needle shield from a syringe having a needle, comprising:
a) providing a needle shield remover comprising a body having a proximal end, a distal end, a proximal portion situated closer to the proximal end than to the distal end, and a distal portion situated closer to the distal end than to the proximal end, the body being configured so that the distal portion moves between a contracted configuration and an expanded configuration in response to opposite movement of the proximal portion, the distal portion having an internal opening for receiving and at least partially surrounding the needle shield therein, an anchor extending inwardly from the distal portion into engagement with the needle shield when the distal portion is in the contracted configuration to secure the body to the needle shield; and
a sleeve in fixed axial engagement with the proximal portion of the body thereby maintaining the distal portion of the body in the contracted configuration such that force applied to the sleeve away from the body removes the needle shield and body from the syringe, wherein the body is moveable with respect to the needle shield when the body is in the expanded configuration and is fixed to the needle shield when the body is in the contracted configuration;
b) positioning a needle shield within a shield puller body while a distal end of the shield puller body is in an expanded state;
c) moving the distal end of the shield puller body from the expanded state to a contracted state thereby coupling the distal end of the shield puller body to the needle shield;
d) slidingly receiving a proximal end of the shield puller body with a sleeve, thereby securing the distal end of the shield puller body in the contracted state; and
e) applying an axial force to the sleeve away from the distal end of the shield puller body, thereby applying the force to the shield puller body and the needle shield to remove the needle shield from the syringe.

17. The method of claim 16, further comprising:
prior to positioning step a), applying a compressive force to the proximal end of the shield puller body to move the distal end of the shield puller body from the contracted state to the expanded state.

18. The method of claim 17, wherein the positioning step b) includes releasing the compressive force from the proximal end of the shield puller body to transfer the distal end of the shield puller body from the expanded state to the contracted state and wherein the coupling step includes at least one of inserting a barb from the shield puller body into the surface of the needle shield and positioning a spur on a distal end of the shield puller body adjacent a distal end of the needle shield.

19. The method of claim 16, wherein the slidingly receiving step c) includes aligning a key on one of the sleeve and shield puller body with a keyway on the other of the sleeve and shield puller body; and positioning the key in the keyway as the shield puller body is slidingly received with the sleeve.

20. The needle shield remover of claim 2, wherein the body is moveable from the contracted configuration to the expanded configuration by applying a compressive force to the proximal portion of the body.

21. The needle shield remover of claim 5, wherein the body is moveable from the contracted configuration to the expanded configuration by applying a compressive force to the proximal portion of the body.

22. The needle shield remover of claim 9, wherein the body is moveable from the contracted configuration to the expanded configuration by applying a compressive force to the proximal portion of the body.

23. The needle shield remover of claim 10, wherein the body is moveable from the contracted configuration to the expanded configuration by applying a compressive force to the proximal portion of the body.

24. The needle shield remover of claim 11, wherein the body is moveable from the contracted configuration to the expanded configuration by applying a compressive force to the proximal portion of the body.

25. The method of claim 16, wherein the body is moveable from the contracted configuration to the expanded configuration by applying a compressive force to the proximal portion of the body.

* * * * *